(12) United States Patent
Ryan et al.

(10) Patent No.: US 8,885,156 B2
(45) Date of Patent: Nov. 11, 2014

(54) APPARATUS AND METHOD FOR DETERMINATION OF TEAR OSMOLARITY

(75) Inventors: Thomas E. Ryan, Batavia, NY (US); George S. Baggs, Amherst, NY (US); Timothy Levindofske, Orchard Park, NY (US)

(73) Assignee: Reichert, Inc., Depew, NY (US)

( * ) Notice: Subject to any disclaimer, the term of this patent is extended or adjusted under 35 U.S.C. 154(b) by 4 days.

(21) Appl. No.: 13/128,260

(22) PCT Filed: Aug. 24, 2010

(86) PCT No.: PCT/US2010/046472
§ 371 (c)(1),
(2), (4) Date: May 9, 2011

(87) PCT Pub. No.: WO2011/028519
PCT Pub. Date: Mar. 10, 2011

(65) Prior Publication Data
US 2011/0211189 A1 Sep. 1, 2011

Related U.S. Application Data

(60) Provisional application No. 61/237,033, filed on Aug. 26, 2009.

(51) Int. Cl.
| | | |
|---|---|---|
| *G01N 21/00* | (2006.01) | |
| *G01N 21/31* | (2006.01) | |
| *A61B 3/10* | (2006.01) | |
| *G01N 21/33* | (2006.01) | |
| *G01N 21/43* | (2006.01) | |

(52) U.S. Cl.
CPC .............. *A61B 3/101* (2013.01); *G01N 21/31* (2013.01); *G01N 21/33* (2013.01); *G01N 2021/434* (2013.01); *G01N 21/43* (2013.01)
USPC .............................................. 356/73

(58) Field of Classification Search
USPC .................................................. 356/72–73
See application file for complete search history.

(56) References Cited

U.S. PATENT DOCUMENTS 5,696,580 A 12/1997 Kubo et al.
6,628,382 B2 9/2003 Robertson
(Continued)

FOREIGN PATENT DOCUMENTS

EP 2088422 8/2009
WO 2004038389 5/2004

OTHER PUBLICATIONS

The International Bureau of WIPO, International Preliminary Report on Patentability issued Feb. 28, 2012 in International Application No. PCT/US2010/046472.

(Continued)

*Primary Examiner* — Abdullahi Nur
(74) *Attorney, Agent, or Firm* — Hodgson Russ LLP

(57) ABSTRACT

An apparatus comprises a spectrophotometer system configured to measure light absorbance by a tear sample, a refractometer system configured to measure refractive index of the tear sample, and an evaluation unit programmed to calculate an osmolarity of the tear sample based on the measured absorbance and refractive index and stored calibration curves. The spectrophotometer and refractometer systems may share a common prism contacted by the tear sample during measurement. The evaluation unit may be programmed to carry out steps of a method for determining osmolarity of the tear sample in accordance with the invention. The osmolarity of the tear sample may be used as an indicator in diagnosing dry eye.

26 Claims, 10 Drawing Sheets

(56) References Cited

U.S. PATENT DOCUMENTS

| | | |
|---|---|---|
| 6,809,826 B2 | 10/2004 | Robertson |
| 7,148,968 B2 * | 12/2006 | Codner et al. ............... 356/445 |
| 7,395,103 B2 | 7/2008 | Cappo et al. |
| 2003/0020915 A1 | 1/2003 | Schueller et al. |
| 2003/0048432 A1 | 3/2003 | Jeng et al. |
| 2005/0159657 A1 * | 7/2005 | Cappo et al. ................ 600/315 |
| 2008/0058627 A1 | 3/2008 | Hernandez |
| 2009/0005660 A1 | 1/2009 | Cappo et al. |

OTHER PUBLICATIONS

Craig; OcuSense, Inc., TearLab Osmolarity System, Section VI 510(k) Summary, May 5, 2009: 10 pages.

Craig et al.; Refractive Index and Osmolarity of Human Tears; Optometry and Vision Science, vol. 72, No. 10, pp. 718-724.

Written Opinion of the International Searching Authority for PCT/US2010/046472 dated Mar. 3, 2011 for Reichert, Inc. et al.; 8 pages.

Casassa et al., Partial Specific Volumes and Refractive Index Increments in Multicomponent Systems 1, The Journal of Physical Chemistry, vol. 65, No. 3, pp. 427-433. Mar. 1, 1961.

* cited by examiner

APPARATUS AND METHOD FOR DETERMINATION OF TEAR OSMOLARITY

CROSS-REFERENCE TO RELATED APPLICATIONS

The present application claims priority benefit of U.S. Provisional Patent Application No. 61/237,033 filed Aug. 26, 2009, the entire disclosure of which is incorporated herein by reference.

FIELD OF THE INVENTION

The present invention relates generally to devices and methods for diagnosing "dry eye" in patients. More particularly, the invention relates to devices and methods for analyzing tear fluid samples to determine tear fluid osmolarity due to salinity, and protein concentration in tear fluid, as indicators of dry eye.

BACKGROUND OF THE INVENTION

Dry eye disease has been estimated to affect from 5% through 30% of the population depending on age and diagnostic criteria. Common tests for dry eye are subjective (e.g. questionnaires) or invasive (e.g. Schirmir Test, Tear Breakup Time, Vital Staining). More complex technologies are not simple or rapid enough to be useful as a screening test (protein levels, interferometry). In general, the repeatability of common tests for dry eye is not very good. A 2004 study of dry eye patients concluded the repeatability of objective slit lamp tests was poor and Schirmir test readings "fluctuate severely" from visit to visit. A 2008 review describes problems with variability and reproducibility of common dry eye disease diagnostic tests.

The International Dry Eye Workshop (2007) defined dry eye as "a multifactorial disease of the tears and ocular surface that results in symptoms of discomfort, visual disturbance and tear film instability with potential damage to the ocular surface. It is accompanied by increased osmolarity of the tear film and inflammation of the ocular surface."

The present invention specifically addresses the "increased osmolarity" described in the definition. The International Dry Eye Workshop (2007) recognized hyperosmolarity as an attractive "signature feature" of dry eye disease. Tomlinson et al. describe tear osmolarity as "[a] single biophysical measurement that captures the balance of inputs and outputs from the tear film dynamics." A. Tomlinson et al., "Tear Film Osmolarity: Determination of a Referent for Dry Eye Diagnosis," *Investigative Ophthalmology and Vision Science*, vol. 47, pages 4309-4315 (2006). The first studies of individual tear fluid osmolarity were reported in 1978. These reports used freezing point and dew point depression to determine osmolarity and found significant differences between normal and dry eye disease patients. Numerous studies since 1978 have confirmed osmolarity is a key parameter in the diagnosis of dry eye disease. Osmolarity has been discussed as the new "Gold Standard" in diagnosing dry eye disease as early as 1986 and as recently as 2007.

Objective osmolarity tests of tear fluid are possible, however they have seen limited use in the diagnosis of dry eye due to difficulties in making the measurements on sub-microliter samples, the high level of technical competency required and the limited availability of instruments to health care practitioners. Technologies used for determining tear osmolarity include freezing point depression, vapor pressure (dew point) and conductivity. A common problem with these tests is the very broad and overlapping normal distributions seen in comparing normal and dry eye subjects. Typical averages and standard deviations observed in osmolarity tests as summarized by Tomlinson et al. are shown in Table 1.

TABLE 1

| Test | Normal Subjects | Dry Eye Subjects |
| --- | --- | --- |
| Freezing Point Depression | 304.4 +/− 7.2 | 329.6 +/− 17 |
| Conductivity | 296.4 +/− 30 | 324 +/− 41 |
| Average from 16 references | 302 +/− 9.7 | 326.9 +/− 22.1 |

Preliminary data is also available on a newer conductivity based "lab on a chip" instrument from Tearlab Corporation (San Diego, Calif.). The Food and Drug Administration (FDA) 510(k) Performance Testing Summary for this instrument shows a normal range of 294+/−5.5 and moderate dry eye range of 316+/−4.5. This data was generated using "contrived tear" samples with constant salts, protein and lipid. Additional variation was seen between instruments, sites and within and between lot variation in the disposable lab-on-a-chip collection/electrode device.

U.S. Pat. No. 7,395,103 B2 describes a surface plasmon resonance (SPR) device for determining tear osmolarity. SPR-based sensors use a gold surface to contact and read the refractive index of the sample. No data is currently available for this instrument. It is well known that proteins quickly adsorb to metallic surfaces used for SPR. The signal from this device would thus be a combination of the bulk (solution) refractive index and the adsorbing protein.

Measuring the refractive index of tear fluid by critical angle refractometry alone has been previously proposed and tested as a method to measure tear osmolarity See J. P. Craig et al., "Refractive Index and Osmolality of Human Tears," *Optometry and Vision Science*, vol. 72, pages 718-724 (1995). The correlation between refractive index and osmolarity is well established for salt solutions. Craig et al. found no correlation between refractive index and osmolarity measured by freezing point depression and a slight correlation between lactoferrin concentration and refractive index. No attempts were made to correct the refractive index reading for changing protein concentration.

The relatively high variability observed when measuring tear osmolarity is likely due to a number of factors including those inherent in the measuring technology and those contributed by the sample. Instruments which measure freezing point depression and vapor pressure require very accurate temperature measurements in an environment where temperature is changing rapidly. Conductivity measurements require the sample be brought into contact with electrodes and an electrical current passed through the sample. Conductivity measurements are also both temperature and volume dependent.

It is highly likely that sample composition plays an important role in the variability of tear fluid measurements. Tears are complex mixtures of many solutes, the vast majority of which are salts (NaCl; KCl) and proteins. Dissolved salts and proteins contribute approximately equally to the total solute mass of the tear. Osmolarity is a function of the molar concentration or number of molecules of a solute per volume of solution. Because of their large mass and relatively low molarity, proteins have a greatly diminished effect on tear osmolarity relative to salts, which have higher molar concentrations in tear fluid; at equal mass, the effect of proteins on osmolarity is on the order of 1,000 fold less than the effect of salts. The effect of samples with varying protein concentrations on both conductivity and freezing point/vapor pressure measurements is not well understood and is a likely candidate for a part of the observed variability. A 2004 study concluded significant errors were introduced when protein concentration was varied during conductivity based hemoglobin and hematocrit assays. Proteins also have a tendency to coat and bind to metallic surfaces fairly quickly. Electrode "fouling" is a common occurrence when measuring the conductivity of protein containing solutions. Measurement errors are the result of a high resistance and/or electrochemical reactions on coated metallic electrodes.

Thus, there is a need for an apparatus and a method capable of accurately and precisely measuring tear fluid osmolarity. The apparatus and method should be easy to use with respect to sub-microliter tear fluid samples.

SUMMARY OF THE INVENTION

The present invention uses optical measurement techniques to measure refractive index and absorbance of a tear sample, and determines osmolarity based on these measurements. The refractive index of a solution is directly proportional to the total mass of solute in a sample. The refractive index of tear fluid is indicative of both salinity and dissolved protein in the tear fluid. Dissolved proteins and salts contribute approximately equally to the measured refractive index of tear fluid. A refractive index measurement provided by the present invention is thus the sum of salt, protein, and the water refractive index components of the tear sample. The absorbance measurement provides an independent measurement of protein concentration in the tear sample. Once the protein concentration is determined, it may be converted to a refractive index increment which may then be subtracted from the overall measured refractive index of the sample. The measured refractive index minus the refractive index increment due to protein equals the refractive index due to salinity alone. The relationship between refractive index and salt concentration is essentially linear in the applicable concentration range. Accordingly, the refractive index of the tear sample due to salinity alone serves as a direct indicator of salt concentration, the major contributor to tear osmolarity.

An apparatus of the present invention generally comprises an absorbance detection system (spectrophotometer system) configured to measure light absorbance by the tear sample, a refractometer system configured to measure refractive index of the tear sample, and an evaluation unit programmed to calculate an osmolarity of the tear sample based on the measured light absorbance and the measured refractive index. In an embodiment of the invention, the evaluation unit is programmed to i) determine a protein concentration of the tear sample corresponding to the measured light absorbance; ii) determine a protein refractive index increment corresponding to the protein concentration of the tear sample; iii) calculate a refractive index of the tear sample due to salinity alone by computing a difference between the measured refractive index of the tear sample and the protein refractive index increment; iv) determine a salt concentration of the tear sample corresponding to the refractive index of the tear sample due to salinity alone; and v) convert the salt concentration to an osmolarity of the tear sample.

The spectrophotometer system and the refractometer system share a prism, and the prism has a prism surface to be contacted by the tear sample.

The spectrophotometer system includes a light source, for example a UV light emitting diode, and a corresponding light detector for receiving light transmitted through the tear sample. In one embodiment, the light source is positioned in a base of the apparatus and the light detector is fixed to a hinged cover that closes over the prism. In another embodiment, the light source is fixed to the hinged cover and the light detector is positioned in the base. The spectrophotometer system further includes a transparent window positionable relative to the prism such that a sample-contacting surface of the window is substantially parallel to the prism surface for defining a layer of tear sample having uniform thickness.

The refractometer system includes a light source and optics arranged to illuminate an interface between the prism surface and the tear sample with rays at various angles of incidence within a predetermined range of angles that includes a critical angle of total internal reflection of the prism-sample interface. The refractometer system further includes a photodetector array arranged to receive light after interaction at the prism-sample interface, whereby the location of a shadowline on the array is indicative of the refractive index of the tear sample.

The evaluation unit is programmed and configured to determine osmolarity of the tear sample based on measurements made by the spectrophotometer system and the refractometer system, making reference to calibration curves stored in memory. The determined osmolarity may be used as an indicator in the diagnosis of dry eye.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
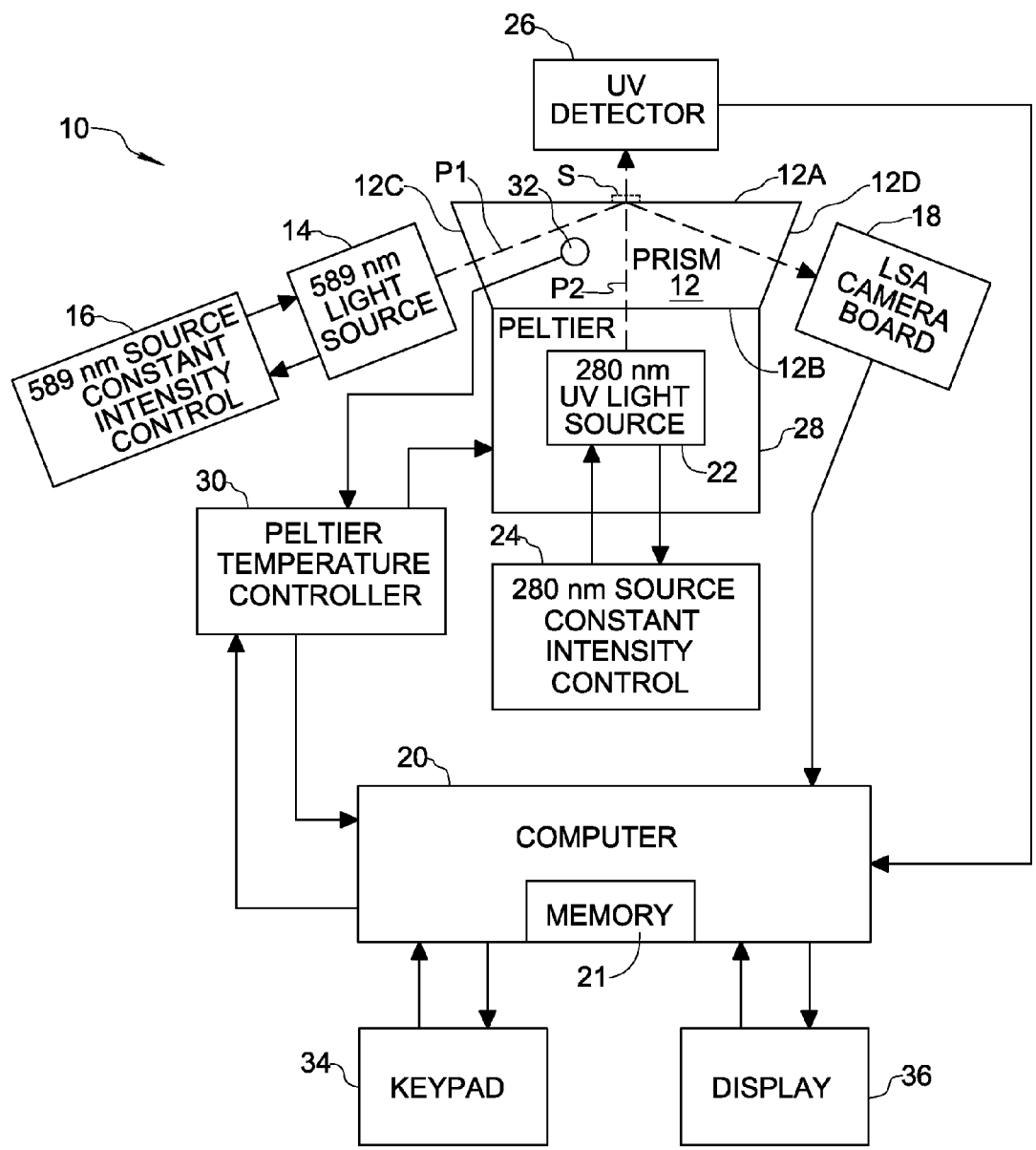
FIG. 1 is a schematic block diagram of an apparatus for analyzing a sample of tear fluid formed in accordance with an embodiment of the present invention.
Figure 2:
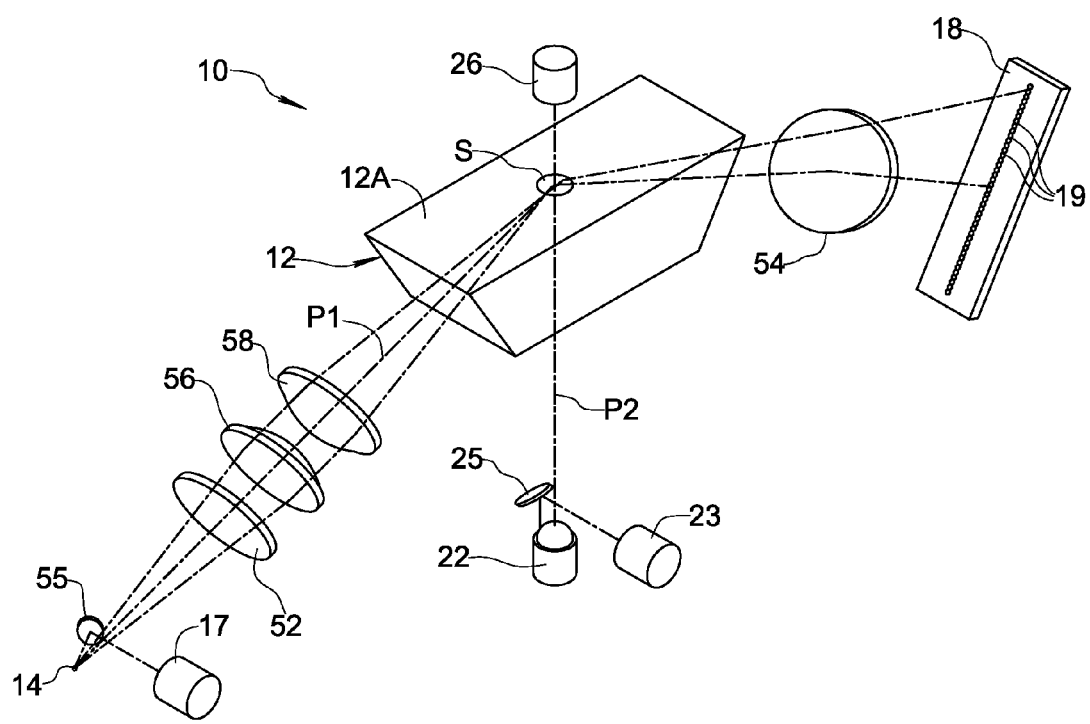
FIG. 2 is an optical schematic diagram of the apparatus shown in FIG. 1.

FIGS. 1 and 2 schematically show an apparatus 10 formed in accordance with an embodiment of the present invention.

Apparatus 10 operates to measure osmolarity of a tear fluid sample S as an indicator of dry eye. The volume of tear fluid sample S may be on the order of 250 nanoliters.

Apparatus 10 comprises an optical prism 12 having a top surface 12A on which tear sample S is placed for analysis. Prism 12 is preferably a high refractive-index prism and is shared by a spectrophotometer system (also referred to herein as an "absorbance detection system") and a refractometer system of apparatus 10, each system being described in detail below. For example, prism 12 may be a sapphire prism having a refractive index of about 1.76. Prism 12 may be a trapezoidal prism having parallel top and bottom surfaces 12A, 12B and nonparallel side surfaces 12C, 12D.

Figure 3:
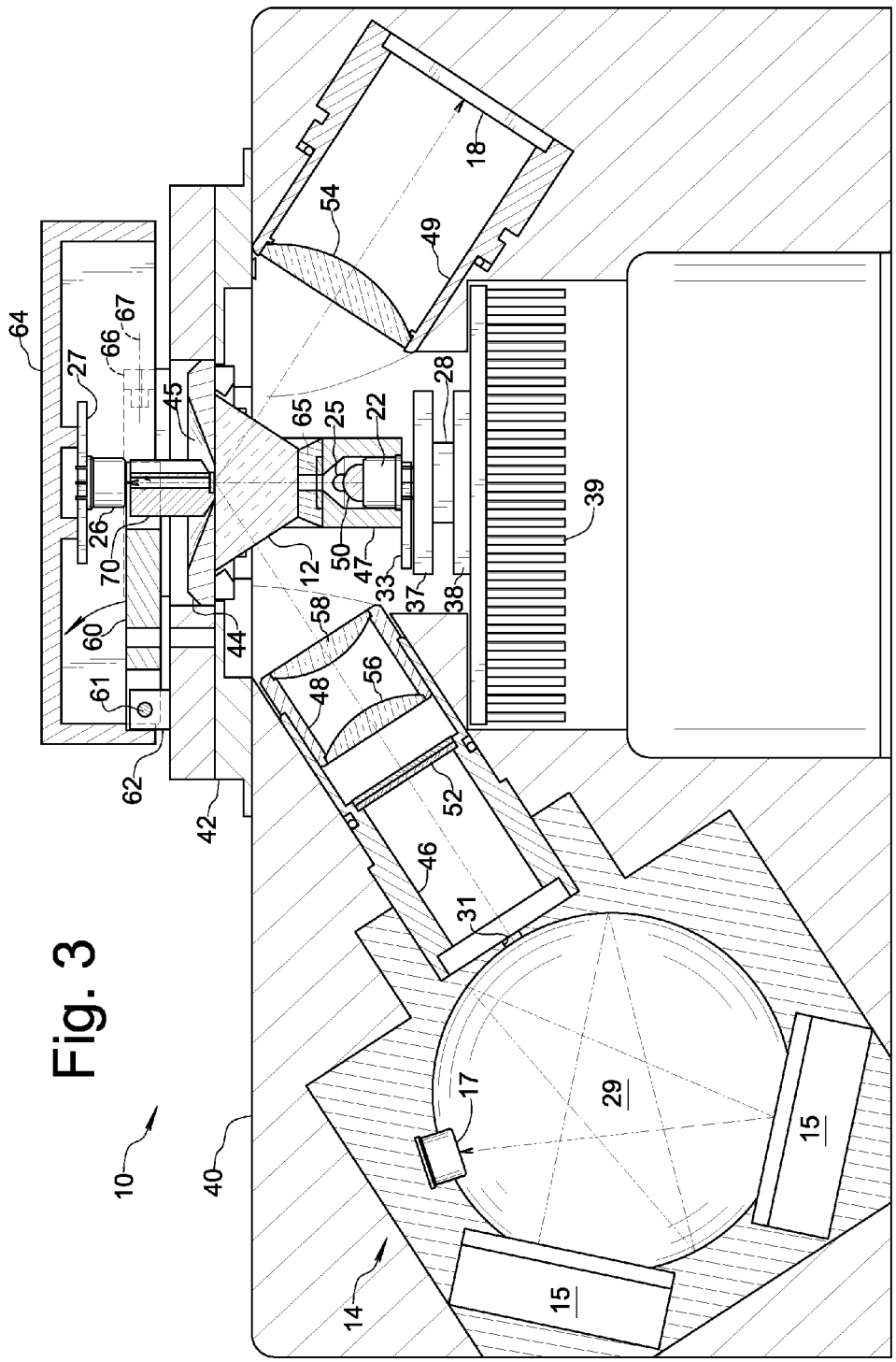
FIG. 3 is a partially sectioned view of the apparatus shown in FIGS. 1 and 2.
Figure 4:
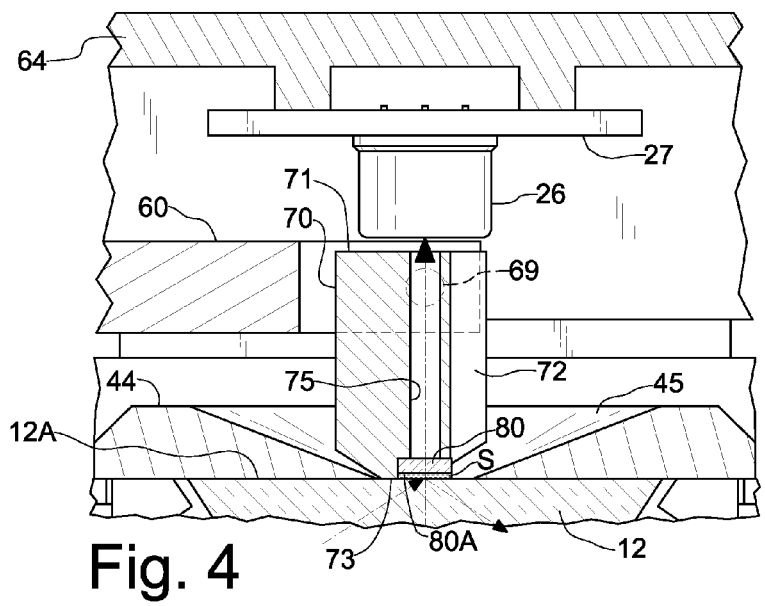
FIG. 4 is an enlarged view showing a sample interface of the apparatus shown in FIG. 3.
Figure 5:
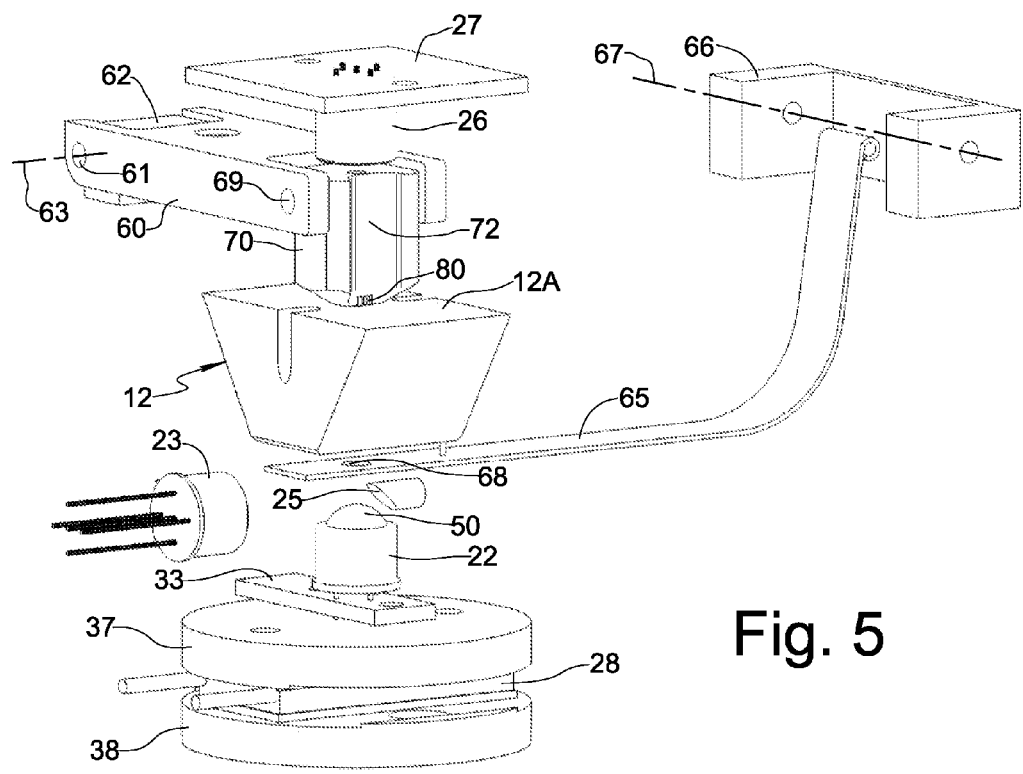
FIG. 5 is a perspective view showing an arrangement of components of a spectrophotometer system of the apparatus.

Reference is also made now to FIGS. 3-5. The spectrophotometer system of apparatus 10 is configured to measure light absorbance by tear sample S. In the embodiment shown in FIGS. 1-4, the spectrophotometer system generally includes prism 12 contacted on surface 12A by tear sample S, a light source 22, and a light detector 26 arranged and configured to receive light from source 22 traveling along optical path P2 that is transmitted through tear sample S and prism 12. As will be understood, a portion of the light flux from source 22 is absorbed by sample S and the other transmission media (e.g. prism 12). Therefore, assuming the incident light is of constant intensity, the signal generated by light detector 26 will vary depending upon the absorbance (optical density) of tear sample S at the measurement wavelength, for example at 280 nm. The output signal generated by detector 26 is delivered to a computer 20 including or coupled with one or more memory devices. Computer 20, which may be embedded in apparatus 10 or linked to apparatus 10 through a communications port, includes circuitry configured and programmed to convert the signal from detector 26 to digital form and calculate an absorbance value for tear sample S based on the digitized signal. By way of example, light detector 26 may be a photodiode generating an analog voltage signal as output, and this voltage signal may be measured to 1 millivolt resolution so as to measure optical absorbance to five decimal places.

In the present embodiment, light source 22 is a light-emitting diode (LED) selected to emit UV light in a narrow wavelength band at 280 nm, however another wavelength, multiple wavelengths, or a broader wavelength band could be used without straying from the invention. In order to maintain the illuminating light flux at constant intensity to improve measurement accuracy and precision, a constant intensity control circuit 24 may be arranged and configured to detect a portion of the light flux emitted by light source 22 and adjust energizing current to the light source 22 depending upon the detected flux. The spectrophotometer system may also include means for controlling the temperature of light source 22 to stabilize the wavelength and direction of the emitted light beam. In the embodiment shown in FIG. 1, the temperature control means includes a Peltier element 28 thermally coupled to light source 22, a Peltier temperature controller 30 connected to the Peltier element and to computer 20, and a temperature sensor 32 associated with prism 12 to provide a feedback signal to Peltier controller 30.

The refractometer system of apparatus 10 is configured to measure a refractive index of tear sample S. In the embodiment shown in FIGS. 1 and 2, the refractometer system generally includes prism 12 contacted on surface 12A by tear sample S, a light source 14 emitting light in a narrow wavelength band, for example at 589 nm, and a photodetector array 18. A beam from light source 14 is directed along optical path P1 through surface 12C and into prism 12. The beam may be filtered by a narrow band wavelength filter 52 and focused by lenses 56, 58 at a focal point within prism 12 just below an interface between prism surface 12A and tear sample S. Consequently, the constituent rays of the beam are divergent when they reach the prism/sample interface so as to illuminate the interface with light at various angles of incidence within a predetermined range of angles that includes a critical angle of total internal reflection for the prism sample interface. Light rays incident to the interface at an angle steeper than the critical angle will be refracted and pass out of the system, while the remaining incident rays will be totally internally reflected at the interface and will pass through surface 12D and out of prism 12. For human tear fluid, a suitable range of illumination angles may be approximately from 61 degrees through 65 degrees.

Photodetector array 18, which may be embodied as a linear scanned array (LSA) of individual photodiode elements 19 on a circuit board, is arranged to receive the portion of illuminating light that is totally internally reflected at the prism/sample interface. A magnifying lens 54 may be arranged upstream from photodetector array 18 between prism surface 12D and the photodetector array to magnify the image corresponding to a refractive index range of about 1.33 (water) through 1.37 typical of tear samples, thereby enabling refractive index readings to six decimal places. As will be understood, a shadowline will be imaged on photodetector array 18. Under Snell's Law, the location of the shadowline on photodetector array 18 is indicative of the refractive index of tear sample S. The output signal information generated by photodetector array 18 is delivered to computer 20. Computer 20 converts the signal information from the elements of photodetector array 18 to digital form, and is programmed to determine the location of the shadowline and compute the refractive index of tear sample S based on the shadowline location. The refractometer system itself uses principles well-known to those skilled in the art, and refractometer systems configured substantially in accordance with the above general description are found in the AR700 Automatic refractometer manufactured by Reichert, Inc., assignee of the present application.

Similar to light source 22 of the spectrophotometer system, light source 14 of the refractometer system may have an associated intensity control circuit 16 to maintain the illuminating light flux of the refractometer system at constant intensity. Circuit 16 may be arranged and configured to detect a portion of the light flux from light source 14 and adjust energizing current to light source 14 depending upon the intensity of the detected flux.

As depicted schematically in FIG. 1, apparatus 10 may further comprise a keypad 34 and a display 36, each in communication with computer 20.

FIG. 3 is a partially sectioned view of apparatus 10. Prism 12 is fixed within a base 40 having a platform 42, and a stainless steel sample well 44 having a conically tapered opening 45 resides adjacent prism surface 12A to provide access to a central area of prism surface 12A for contact by tear sample S. A cover 64 is attached to platform 42 by a hinge 66 allowing the cover to be selectively pivoted about a hinge axis 67 between a closed position over sample well 44 as depicted in FIG. 3 and an opened position wherein the sample well is exposed to receive a tear sample S. In the embodiment of FIG. 3, cover 64 carries light detector 26 and an associated circuit board 27 which are fixed to an underside of cover 64.

Details of the spectrophotometer system of apparatus 10 are shown in FIGS. 4 and 5. Apparatus 10 further includes a window mount 70 pivotably mounted at one end of a support arm 60 by pivot pins 69, only one pin being visible in FIG. 5. An opposite end of support arm 60 is attached to platform 42 by a hinge 62 to pivot about a hinge axis 63 defined at a pin 61. In the present embodiment, the hinge axis 67 of cover 64 extends in an orthogonal direction relative to the hinge axis 63 of support arm 60, however other arrangements of the hinge axes 67, 63 are possible.

As best seen in the enlarged view of FIG. 4, window mount 70 includes an end surface 73 distal from pivot pins 69. Window mount 70 is movable relative to base 40 by pivoting support arm 60 about hinge axis 63 and by pivoting the window mount itself relative to the support arm. Window mount 70, particularly the portion near end surface 73, is sized to be received through sample well opening 45. As may be understood, end surface 73 is movable into flush engagement against prism surface 12A. Window mount 70 includes an axial passage 75 in which a transparent window 80 is fixed at an axial location slightly recessed from end surface 73. Transparent window 80 has a window surface 80A contacted by tear sample S during measurement. Window surface 80A is parallel to end surface 73, such that when end surface 73 is moved into flush engagement with prism surface 12A, window surface 80A is parallel or substantially parallel to prism surface 12A, thereby defining a layer of tear sample S having uniform thickness. The thickness of the tear sample layer provides a path length through the tear sample for purposes of the spectrophotometer system. In a currently preferred embodiment, transparent window 80 is a quartz window recessed from end surface 73 by a distance of 100 nm to define the thickness of the tear sample layer. Window mount 70 may include a longitudinal slot 72 communicating from passage 75 to the exterior of window mount 70 in the region between transparent window 80 and end surface 73 to permit excess tear fluid to escape when window mount 70 is brought into a measurement position with end surface 73 flush against prism surface 12A.

Returning now to FIG. 3, spectrophotometer light source 22 is housed in a tube 47 and a collimating lens 50 is positioned adjacent light source 22 for providing a collimated illumination beam along optical path P2. The collimated illumination beam passes through surface 12B of prism 12 in a direction normal to prism surface 12A, then exits the prism through surface 12A and enters the uniform layer formed by tear sample S. The beam exits the tear sample layer through transparent window 80 and continues through passage 75 to light detector 26 arranged adjacent another end surface 71 of window mount 70 opposite from end surface 73. Of course, some of the light is absorbed by prism 12, tear sample S, quartz window 80, and air within passage 75.

As mentioned above, constant intensity control circuit 24 may be arranged and configured to detect a portion of the light flux emitted by light source 22 and adjust energizing current to the light source 22 depending upon the detected flux. To detect light flux emitted by light source 22, a secondary light detector 23 is arranged to receive a portion of the emitted light flux diverted by mirror 25. The output signal from secondary detector 23 is delivered as a feedback signal to constant intensity control circuit 24.

Temperature control of light source 22 stabilizes the wavelength and direction of the emitted light. For this purpose, Peltier element 28 is arranged between thermally conductive plates 37, 38 and is controlled by Peltier temperature controller 30 to keep light source 22 at a stable temperature. An air-cooled heat exchanger 39 may be associated with thermally conductive plate 38 to transfer excess heat away from light source 22. Temperature sensor 32 (shown only in FIG. 1) is arranged to provide feedback signal information to Peltier temperature controller 30.

Where light source 22 is a UV light source, safety features may be provided to protect users from exposure to the UV light. For example, a shutter arm 65 may be mechanically linked to hinge 66 such that when cover 64 is closed, an opening 68 in the shutter arm is aligned on optical path P2 to permit light to pass to light detector 26, and when cover 64 is opened, shutter arm 68 moves with respect to optical path P2 to block UV light. Alternatively, or additionally, an electromechanical switch (not shown) may be configured to automatically shut off light source 22 when cover 64 is opened.

In the present embodiment, refractometer light source 14 comprises a pair of LED arrays 15 arranged to emit light into a light-integrating sphere 29 housed in base 40. By way of example, light-integrating sphere 29 may have an inner diameter of 5.08 cm and a barium sulfate internal coating. By way of further example, LED arrays 15 may be chosen to emit light at 589 nm. Illuminating light escapes light-integrating sphere 29 through a pinhole aperture 31 and travels through wavelength filter 52 and focusing lenses 56, 58. Filter 52, which is matched to the nominal emission wavelength of LED arrays 15 (e.g. 589 nm), may be mounted in an optical tube 46 in base 40 of apparatus 10. Optical tube 46 may receive a secondary tube 48 carrying focusing lenses 56, 58. The use of LED arrays and an integrating sphere to form a light source is known generally from the SR7000DC surface plasmon resonance instrument manufactured by Reichert, Inc. Those skilled in the art will understand that a wide variety of light source arrangements are possible. Thus, in FIG. 2, light source 14 is represented as a generic point source of light.

Constant intensity control circuit 16, mentioned above, may be arranged and configured to detect a portion of the light flux emitted by light source 14 and adjust energizing current to the light source 14 depending upon the detected flux. To detect light flux emitted by light source 14 in the present embodiment, a secondary light detector 17 may be arranged on an inner surface of integrating sphere 29 to receive a portion of the light flux emitted by LED arrays 15. The output signal from secondary detector 17 is delivered as a feedback signal to constant intensity control circuit 16.

Figure 7:
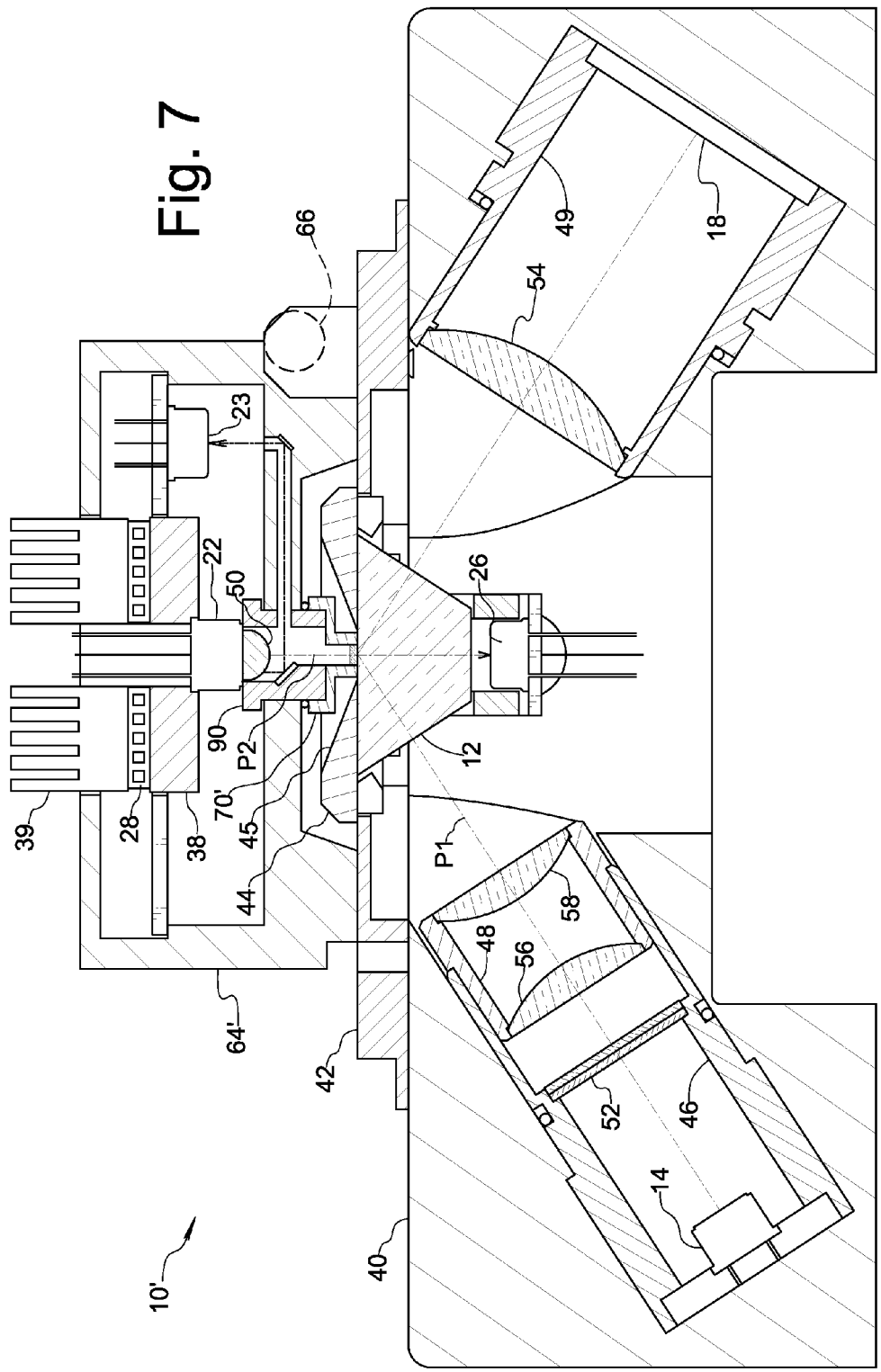
FIG. 7 is a partially sectioned view showing an apparatus for analyzing a sample of tear fluid formed in accordance with another embodiment of the present invention.
Figure 8:
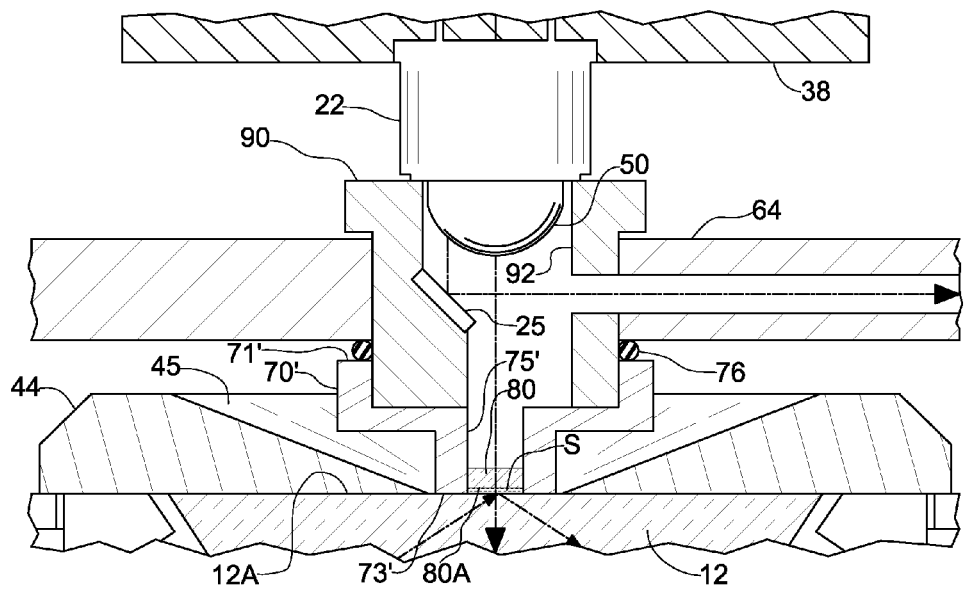
FIG. 8 is an enlarged view showing a sample interface of the apparatus shown in FIG. 7.
Figure 9:
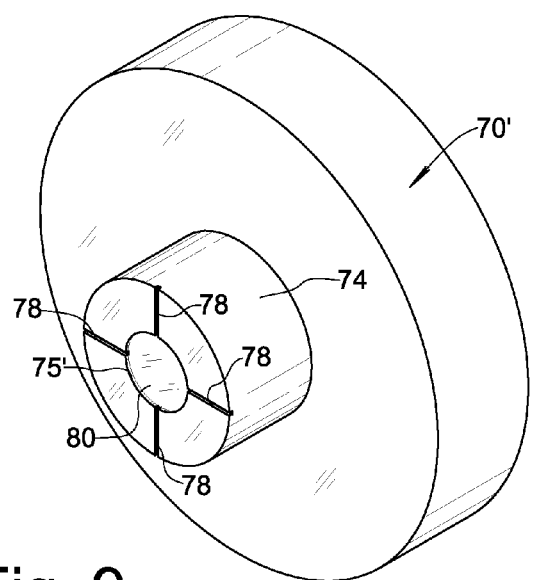
FIG. 9 is a bottom perspective view of a quartz window mounting tube shown in FIGS. 7 and 8.

FIGS. 7-9 illustrate an apparatus 10' formed in accordance with an alternative embodiment of the invention. In the alternative embodiment, the light source 22 of the spectrophotometer system is associated with cover 64, and the light detector 26 of the spectrophotometer system resides in base 40.

FIG. 7 is a partially sectioned view of apparatus 10'. Prism 12 is fixed within base 40, and sample well 44 having conically tapered opening 45 resides adjacent prism surface 12A to provide access to a central area of prism surface 12A for contact by tear sample S. Cover 64 is attached to platform 42 of base 40 by hinge 66 allowing the cover to be selectively pivoted between a closed position over sample well 44 as depicted in FIG. 7 and an opened position wherein the sample well is exposed to receive a tear sample S. Cover 64 carries an optical tube 90 having an axial passage 92, and cover 64 further carries a window mount 70' coaxially arranged on an end of optical tube 90 facing prism surface 12A when cover 64 is closed.

FIGS. 8 and 9 show optical tube 90 and window mount 70' in greater detail. Window mount 70' is fitted onto optical tube 90, and a resilient O-ring 76 is arranged between an end surface 71' of window mount 70' and an underside of cover 64, thereby ensuring flush engagement of an opposite end surface 73' of window mount 70' against prism surface 12A when cover 64 is closed. Window mount 70' includes a reduced-diameter portion 74 and an axial passage 75' in which transparent window 80 is fixed at an axial location slightly recessed from end surface 73'. Reduced diameter portion 74 is sized to fit within sample well opening 45. As in the previous embodiment, transparent window 80 is recessed from end surface 73' by a distance of 100 nm to define the thickness of the tear sample layer. As shown in FIG. 9, end surface 73' of window mount 70' may be provided with radial channels 78 communicating from passage 75' to the exterior of window mount 70' to permit excess tear fluid to escape when window mount 70' is brought into a measurement position with end surface 73' flush against prism surface 12A.

Returning now to FIG. 7, spectrophotometer light source 22 is fixed adjacent a thermally conductive plate 38, and collimating lens 50 is arranged to provide a collimated illumination beam in a downward direction along path P2. As best seen in FIG. 8, the collimated illumination beam passes through transparent window 80 and the uniform layer of tear sample S, and enters prism 12 in a direction normal to prism surface 12A. The beam exits prism 12 through prism surface 12B and is received by light detector 26.

In accordance with the embodiment of FIG. 7, refractometer light source 14 may be a high power LED housed within optical tube 46. Light source 14 is directed to provide an illumination beam along path P1. Other structure of the refractometer system shown in FIG. 7 is similar to that shown in FIG. 3.

Figure 11:
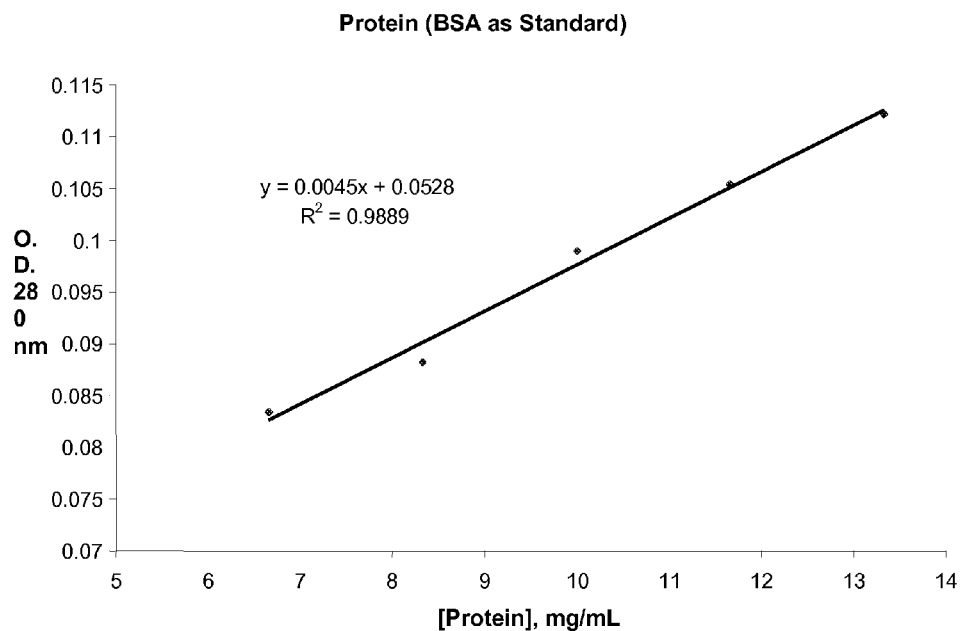
FIG. 11 is an example of a first calibration curve suitable for use in the method shown in FIG. 10.
Figure 12:
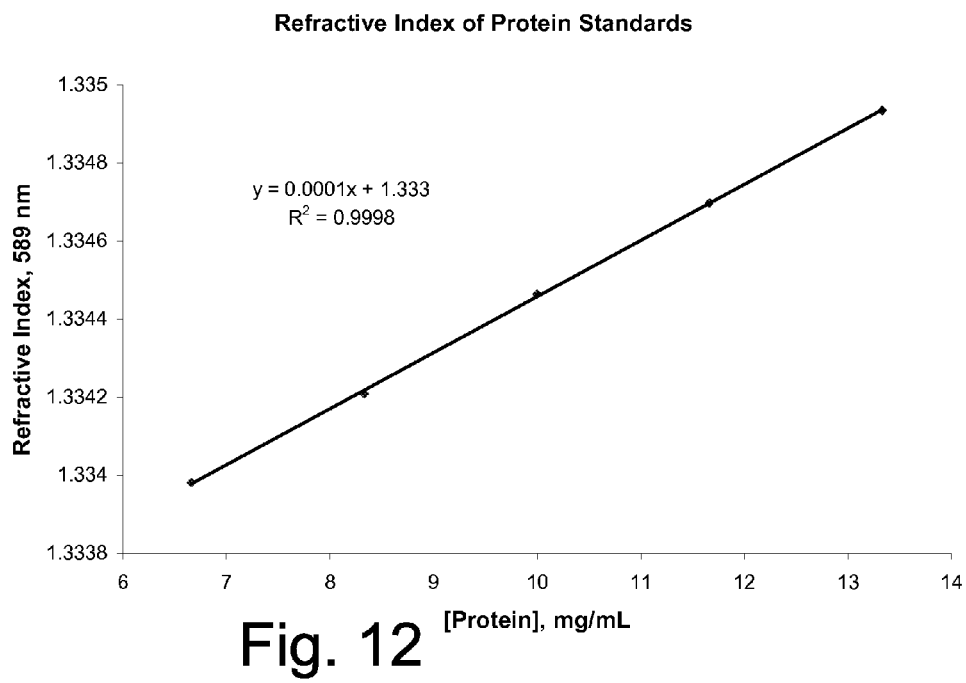
FIG. 12 is an example of a second calibration curve suitable for use in the method shown in FIG. 10.
Figure 13:
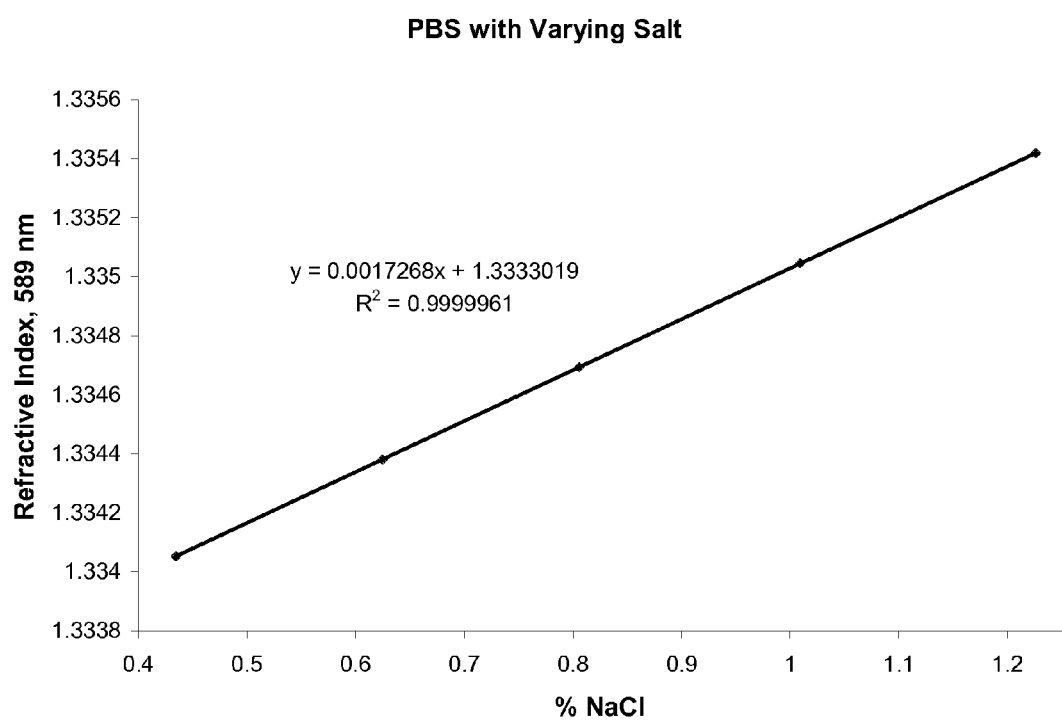
FIG. 13 is an example of a third calibration curve suitable for use in the method shown in FIG. 10.

Reference is again made to the general schematic diagram of FIG. 1. In accordance with an embodiment of the present invention, computer 20 and memory 21 form an evaluation unit programmed and configured to evaluate measurement signals generated by refractometer photodetector array 18 and spectrophotometer light detector 26 and determine an osmolarity value for tear sample S. As part of the evaluation process, computer 20 accesses calibration data stored in memory 21 during preliminary calibration of the apparatus. The calibration steps are described below in connection with FIGS. 11-13. A method by which the detector signal information may be evaluated to determine osmolarity according to an embodiment of the invention is described now with reference to FIG. 10 and is generally identified by reference numeral 100.

Block 110 of method 100 indicates the step of measuring an optical absorbance of tear sample S, for example absorbance at the UV wavelength 280 nm. The absorbance is inversely proportional to the amplitude of the signal generated by light detector 26. The analog signal from light detector 26 is converted to digital form, and the peak amplitude of the digitized signal is read and stored in memory 21.

Block 120 represents the step of measuring a refractive index of tear sample S, denoted herein as $RI\_{TEAR}$. As mentioned above, the location of a shadowline on photodetector array 18 is indicative of the sample refractive index. In accordance with processing steps well known in the art of automatic refractometers, photodetector array 18 is scanned to pull signal information generated by the individual array elements 19, and the signal information is converted to digital form and evaluated to determine a shadowline location. Further in accordance with well known processing steps, the shadowline location is correlated to a refractive index value for tear sample S.

Figure 10:
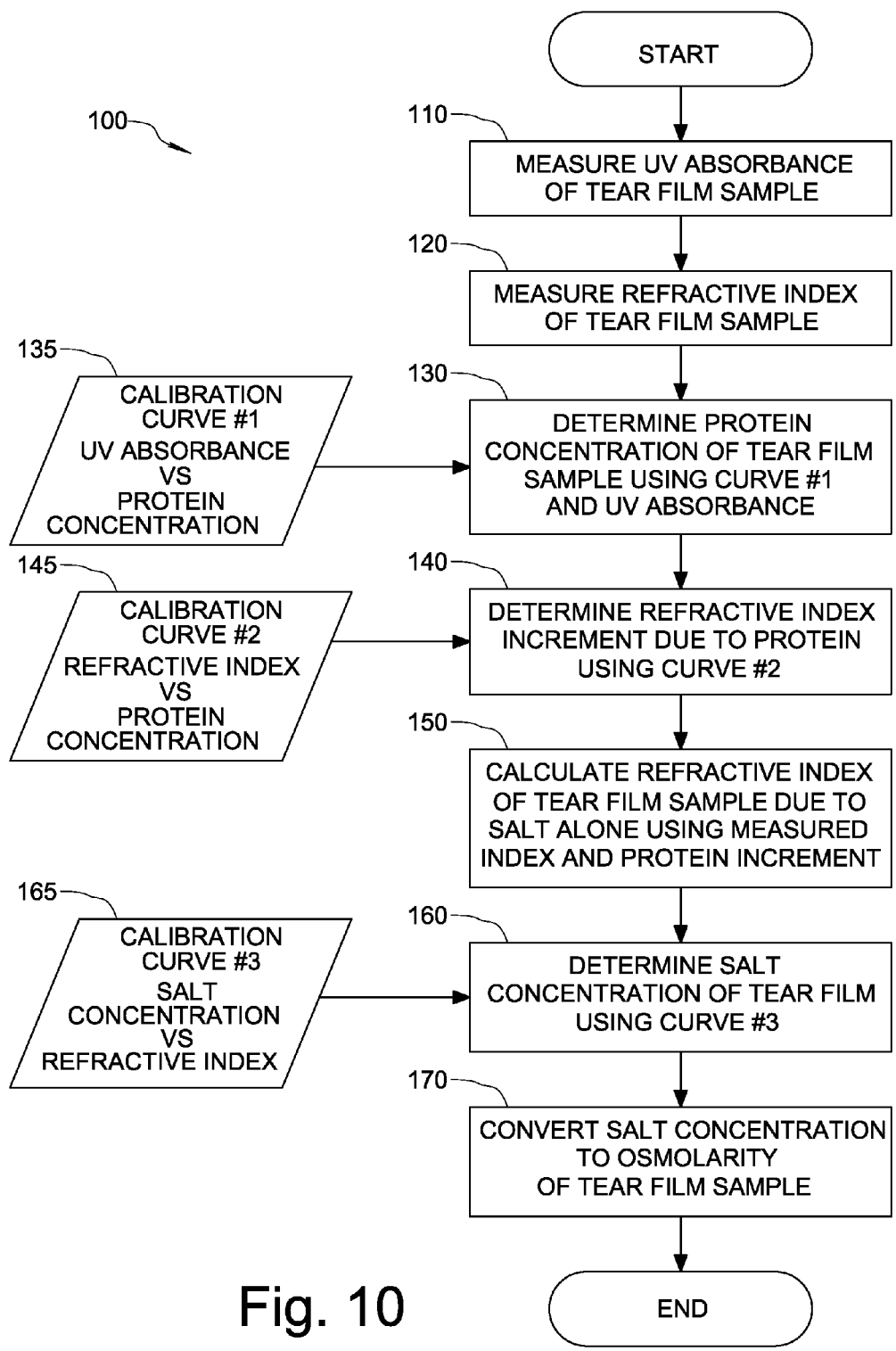
FIG. 10 is flow diagram of a method for analyzing a sample of tear fluid in accordance with a further embodiment of the present invention.

Flow proceeds to block 130, wherein the optical absorbance value ascertained in block 110 is used to determine a protein concentration of tear sample S. The protein concentration may be determined by comparing the measured absorbance value to a stored calibration curve of the relationship between absorbance and protein concentration. An example of this relationship for absorbance of 280 nm UV illumination is plotted in graphical format in FIG. 11 and the relationship is referred to herein as Calibration Curve #1. As may be seen, UV absorbance increases linearly with protein concentration. Calibration Curve #1 may be established by using apparatus 10 to make UV absorbance measurements of standard protein solutions having known protein concentrations. By way of example, Calibration Curve #1 shown in FIG. 11 was established using bovine serum albumin as a standard in the concentration range normally found in tear fluid. The data in FIG. 11 were taken using a spectrophotometer pathlength of 100 nm. The extremely small volume of collected tear fluid samples necessitates the short pathlength. This short pathlength is also well suited for the relatively high protein concentrations in tear fluid and maintains the absorbance readings well within a linear range relative to protein concentration. Calibration Curve #1 may be stored in memory 21 for access by computer 20. Protein concentration of tear sample S is determined by finding the UV absorbance in Calibration Curve #1 corresponding to the measured UV absorbance of tear sample S, and reading the protein concentration associated with such UV absorbance. In FIG. 10, stored Calibration Curve #1 is represented by block 135.

The next step, represented by block 140, is to determine a protein refractive index increment $RI\_{INCREMENT\_PROTEIN}$ of tear sample S corresponding to the protein concentration of the tear sample determined in block 130. The protein refractive index increment $RI\_{INCREMENT\_PROTEIN}$ is the incremental contribution to the refractive index of a protein solution attributed to the protein component of the solution, and is calculated by finding the difference between the overall refractive index of a protein solution and the refractive index of water. The refractive index of water at 20° C. and 589 nm is 1.332987.

To determine the protein refractive index increment of tear sample S, the protein concentration of the tear sample S obtained in block 130 may be referenced to a second stored calibration curve that represents the relationship between protein concentration and refractive index of protein solutions. An example of this relationship is plotted in graphical format in FIG. 12 and the relationship is referred to herein as Calibration Curve #2. By way of example, Calibration Curve #2 shown in FIG. 12 was established at 589 nm and 20° C. using bovine serum albumin as a standard in the concentration range normally found in tear fluid. As may be seen, refractive index increases linearly with protein concentration. A refractive index corresponding to the protein concentration of tear sample S is read from Calibration Curve #2 and the refractive index of water is subtracted therefrom to yield a protein refractive index increment $RI\_{INCREMENT\_PROTEIN}$ for the tear sample. As an alternative, the refractive index of water could be subtracted out in establishing Calibration Curve #2 so that Calibration Curve #2 directly relates protein refractive index increment to protein concentration, thereby enabling protein refractive index increment $RI\_{INCREMENT\_PROTEIN}$ to be read directly from Calibration Curve #2. In FIG. 10, stored Calibration Curve #2 is represented by block 145.

Flow proceeds to block 150 in FIG. 10, wherein the refractive index of tear sample S due to salinity alone, designated herein as $RI\_{TEAR\_SALT}$, is calculated. The calculation may be carried out by subtracting the protein refractive index increment $RI\_{INCREMENT\_PROTEIN}$ determined in block 140 from the tear sample refractive index $RI\_{TEAR}$ measured in block 120.

The salinity refractive index value $RI\_{TEAR\_SALT}$ calculated in block 150 may then be used to determine the salinity concentration of tear sample S pursuant to block 160 and with reference to a third stored calibration curve represented in FIG. 10 by block 165. The third calibration curve represents the relationship between refractive index of a saline solution and salt concentration of the saline solution. An example of this relationship is plotted in graphical format in FIG. 13 and the relationship is referred to herein as Calibration Curve #3. By way of example, Calibration Curve #3 shown in FIG. 13 was established at 589 nm and 20° C. using phosphate buffered saline solution as a standard with varying salt concentration in the concentration range normally found in tear fluid. As may be seen, refractive index increases linearly with salt concentration. The salt concentration of tear sample S may be determined from Calibration Curve #3 by reading the salt concentration corresponding to the salinity refractive index $RI_{TEAR\_SALT}$ of tear sample S calculated in block 150.

Finally, in block 170, the osmolarity of tear sample S is calculated from the salt concentration of the tear sample determined in block 160. Osmolarity is calculated from salt concentration as follows:

2*Salinity Molarity(Moles/Liter)=Osmolarity(Osmoles/Liter).

The calculated osmolarity may be reported directly by display 36. The osmolarity may also be compared to clinical standards stored in memory 21 correlating osmolarity to dry eye, wherein an osmolarity reading considered indicative of dry eye is flagged or otherwise called to the special attention of a user.

Additions and variations to the apparatus and method are possible. For example, in addition to determining tear osmolarity, the apparatus may also report protein concentration in tear fluid as a screening factor for dry eye. It is generally believed protein levels are slightly reduced in tear fluid associated with dry eye. Lower protein concentration in the tear fluid sample could serve as confirmation of a dry eye diagnosis based on tear osmolarity.

The major protein components in tear fluid are Lysozyme, Lactoferrin, Immunoglobulins and Lipocalin 1 (tear prealbumin). Each of these proteins has a different molar extinction coefficient at 280 nm. This is due to different numbers of the amino acids tryptophan, tyrosine and cysteine. The molar extinction coefficient is proportional to the absorbance contribution of the protein species. Consequently, if a protein with a high molar extinction coefficient were to decrease or increase significantly in the tear fluid, the mass contribution correction may not follow the protein concentration versus absorbance calibration. This could result in an error calculating the refractive index increment due to protein. While this is not likely it is possible. It is unlikely because protein concentrations in tear fluid are not reduced by enough to create a significant error in this screening tool. It may be possible to correct for concentration changes in individual proteins with different molar extinction coefficients in various ways. One way is by reading absorbance at multiple wavelengths. By way of example, miniature spectrophotometer systems having a broad spectrum light source and a diffraction grating or other optical element for dispersing the light into separate wavelength bands for receipt by different regions of a photodiode array are known, such as certain miniature spectrophotometers manufactured by Ocean Optics Inc. of Dunedin, Fla. Another way is by taking an entire UV scan and using the first derivative of the scan to identify significant changes in proteins with high or low extinction coefficients (e.g. 254/280 nm, 260/280 nm ratios). Another way is to use a very broad absorbance illumination bandwidth (e.g. 240 to 280 nm) to average out these effects. Yet another way is to read absorbance at 214 nm, because peptide bonds absorb at 214 nm (this would eliminate variation due to different protein extinction coefficients at 280 nm).

Figure 6:
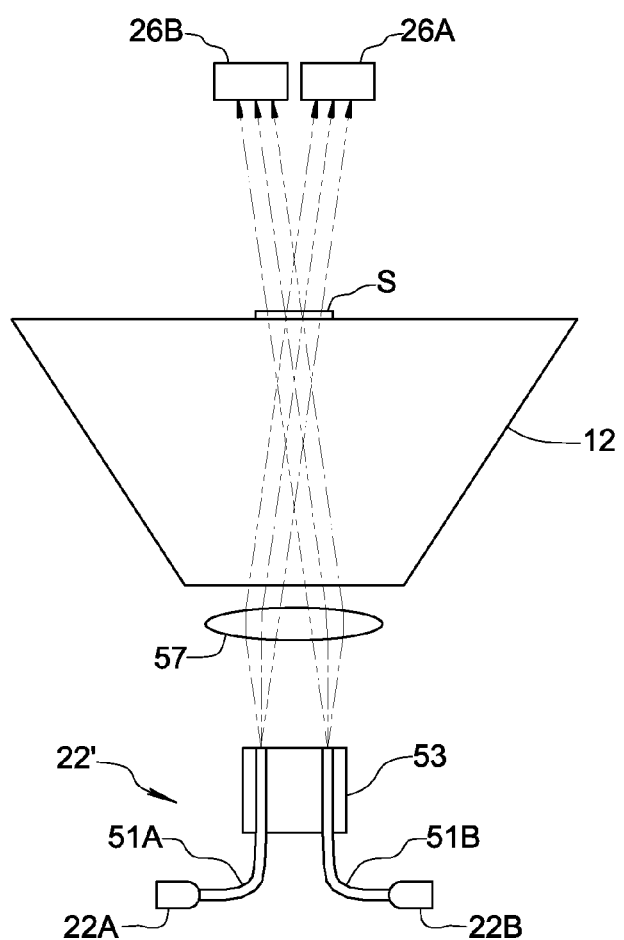
FIG. 6 is an optical schematic diagram showing an alternative spectrophotometer system.

FIG. 6 schematically illustrates an alternative embodiment of the spectrophotometer system wherein tear sample S is illuminated with light at two different wavelengths. A further benefit of a spectrophotometer system using two different wavelengths is that it corrects for possible nucleic acid contamination in the tear sample. As shown in FIG. 6, a light source 22' of the alternative spectrophotometer system includes a first light source 22A and a second light source 22B emitting light at two different wavelengths. For example, light source 22A may be an LED emitting light at a wavelength of 280 nm, and light source 22B may be an LED emitting light at a wavelength of 254 nm. Alternatively, light sources 22A and 22B may emit overlapping or even the same spectral band, and different wavelength selection filters (not shown) may be associated with the light sources to transmit different wavelengths. The light from light sources 22A and 22B may be directed through optical fibers 51A and 51B, respectively, to a fiber array 53 facing sample S. An optical element 57 the different wavelength beams through sample S, and a light detector 26' includes a pair of light detectors 26A and 26B arranged downstream from sample S to respectively receive light from sources 22A and 22B transmitted through sample S. Light detectors 26A and 26B are configured to detect a specific wavelength of light corresponding to the wavelength emitted by its associated light source; i.e. light detector 26A detects light at a wavelength of 280 nm and light detector 26B detects light at a wavelength of 254 nm. While separate optical fibers 51A, 51B are depicted, a coarse optical fiber capable of wavelength-division multiplexing (WDM) may also be used to transmit illumination light having different wavelengths.

In preliminary work related to this invention, it has been observed that the UV absorbance versus pathlength of high molecular weight proteins (e.g. immunoglobulins) is not linear at very short pathlengths such as the 100 nm pathlength described above. This relationship is linear for the three additional lower molecular weight proteins. Therefore, modifying the pathlength may allow for the effect of the high extinction coefficient immunoglobulins to be closely matched with the lower molecular weight, lower extinction coefficient proteins.

Those skilled in the art will understand that optical absorbance and optical transmittance are inversely related properties. Therefore, transmittance is deemed to be equivalent to absorbance in the context of this specification, and reference to absorbance detection is understood to literally cover transmittance detection.

Those skilled in the art will also realize that a transmitted light automatic refractometer system may be substituted for a reflected light automatic refractometer system as described above. In a transmitted light refractometer, light transmitted through the prism-sample interface is detected instead of light totally internally reflected at the prism-sample interface. Such a substitution is within the scope of the present invention.

While the invention has been described in connection with exemplary embodiments, the detailed description is not intended to limit the scope of the invention to the particular forms set forth. The invention is intended to cover such alternatives, modifications and equivalents of the described embodiment as may be included within the spirit and scope of the invention.

LIST OF REFERENCE NUMERALS

10, 10' Apparatus
12 Prism
12A-12D Prism surfaces
14, 14' Refractometer light source
15 LED arrays
16 Constant intensity control for 14, 14'

17 Secondary light detector associated with 14, 14'
18 Refractometer photodetector array
19 Photodiode elements of array 18
20 Computer
21 Memory
22, 22' Spectrophotometer light source
22A, 22B Different wavelength LEDs for 22'
23 Secondary light detector associated with 22
24 Constant intensity control for 22
25 Mirror
26, 26' Spectrophotometer light detector
26A, 26B Spectrophotometer light detectors associated with 22A, 22B
27 Circuit board for 26
28 Peltier element
29 Light-integrating sphere
30 Peltier temperature controller
31 Pinhole aperture in sphere 29
32 Temperature sensor
33 Circuit board for 22
34 Keypad
36 Display
37 Thermally conductive plate
38 Thermally conductive plate
39 Heat exchanger
40 Base
42 Platform
44 Sample well
45 Tapered opening in sample well 44
46 Optical tube
47 Optical tube for light source 22
48 Secondary tube
49 Optical tube
50 Collimating lens after light source 22
51A, 51B Optical fibers
52 Wavelength filter
53 Optical fiber array
54 Magnifying lens
55 Mirror
56 Focusing lens
57 Optical element
58 Focusing lens
60 Support arm
61 Pin
62 Hinge for support arm 60
63 Hinge axis of hinge 62
64, 64' Cover
65 Shutter arm
66 Hinge for cover 64, 64'
67 Hinge axis of hinge 66
68 Opening in shutter arm 65
69 Pivot pins
70 Window mount
71, 71' End surface of 70, 70'
72 Slot in 70
73 End surface of 70
74 Reduced diameter portion of 70'
75, 75' Axial passage through 70, 70'
76 O-ring
78 Radial channels in end surface 73'
80 Transparent window
90 Optical tube for 70'
92 Passage through optical tube 90

What is claimed is:
1. An apparatus for analyzing a sample of tear fluid, the apparatus comprising:
an absorbance detection system configured to measure light absorbance by the tear sample;
a refractometer system configured to measure refractive index of the tear sample; and
an evaluation unit programmed to calculate an osmolarity of the tear sample based on the measured light absorbance and the measured refractive index.

2. The apparatus according to claim 1, wherein the evaluation unit is programmed to i) determine a protein concentration of the tear sample corresponding to the measured light absorbance; ii) determine a protein refractive index increment corresponding to the protein concentration of the tear sample; iii) calculate a refractive index of the tear sample due to salinity alone by computing a difference between the measured refractive index of the tear sample and the protein refractive index increment; iv) determine a salt concentration of the tear sample corresponding to the refractive index of the tear sample due to salinity alone; and v) convert the salt concentration to an osmolarity of the tear sample.

3. The apparatus according to claim 1, wherein the absorbance detection system and the refractometer system share a prism, and the prism has a transparent prism surface to be contacted by the tear sample.

4. The apparatus according to claim 3, wherein the absorbance detection system includes a transparent window, the transparent window has a window surface contacted by the tear sample, and the transparent window is positionable relative to the prism such that the window surface is substantially parallel to the prism surface for defining a layer of tear sample having uniform thickness.

5. The apparatus according to claim 4, further comprising:
a base, wherein the prism is fixed to the base;
a support arm hingedly attached to the base for movement relative to the base about a first hinge axis; and
a window mount coupled to the support arm for movement therewith, wherein the transparent window is mounted in the tubular window support.

6. The apparatus according to claim 5, wherein the window mount is pivotably coupled to the support arm.

7. The apparatus according to claim 5, further comprising a cover hingedly attached to the base for movement relative to the base about a second hinge axis, wherein the absorbance detection system includes a light source and a primary photodetector cooperating with the light source, and one of the light source and the primary photodetector is coupled to the cover for movement therewith.

8. The apparatus according to claim 7, wherein the first hinge axis and the second hinge axis extend in orthogonal directions relative to one another.

9. The apparatus according to claim 4, further comprising:
a base, wherein the prism is fixed to the base;
a cover hingedly attached to the base for movement relative to the base about a hinge axis; and
a tubular window support coupled to the cover for movement therewith, wherein the transparent window is mounted in the tubular window support.

10. The apparatus according to claim 9, wherein the absorbance detection system includes a light source and a primary photodetector cooperating with the light source, wherein one of the light source and the primary photodetector is coupled to the cover for movement therewith.

11. The apparatus according to claim 3, wherein the absorbance detection system includes a light source and a primary photodetector arranged on opposite sides of the prism surface, wherein the primary photodetector receives light from the light source after the light has passed through the tear sample.

12. The apparatus according to claim 11, wherein prism surface is horizontal, and the light source is located under the prism surface.

13. The apparatus according to claim 11, wherein the absorbance detection system further includes a secondary photodetector arranged to receive light from the light source that has not passed through the tear sample.

14. The apparatus according to claim 11, further comprising a Peltier element arranged for thermal control of the light source.

15. The apparatus according to claim 3, wherein the absorbance detection system is configured to measure light absorbance by the tear sample at a plurality of discrete wavelengths.

16. The apparatus according to claim 3, wherein the refractometer system includes an illumination means for illuminating an interface between the prism surface and the tear sample with non-parallel rays and a photodetector array arranged to receive illuminating light totally internally reflected at the interface.

17. An apparatus for analyzing a sample of tear fluid, the apparatus comprising:
- a base;
- a cover movable relative to the base;
- a prism fixed to the base, the prism including a prism surface for contacting the tear sample;
- a first illumination means for illuminating an interface between the first surface of the prism and the tear sample with non-parallel rays;
- a photodetector array arranged to receive illuminating light totally internally reflected at the interface;
- a second illumination means for directing a collimated beam at the tear sample along a path perpendicular to the prism surface, the second illumination means including a light-emitting diode; and
- a photodetector arranged to receive light from the collimated beam transmitted through the tear sample;
- wherein one of the light-emitting diode and the photodetector is fixed to the cover for movement with the cover relative to the base.

18. The apparatus according to claim 17, further comprising a transparent window, having a window surface contacted by the tear sample, wherein the transparent window is positionable relative to the prism such that the window surface is substantially parallel to the prism surface for defining a layer of tear sample having uniform thickness.

19. A method for analyzing a sample of tear fluid, the method comprising the steps of:
- A) measuring an optical absorbance of the tear sample;
- B) measuring a refractive index of the tear sample;
- C) determining a protein concentration of the tear sample corresponding to the measured absorbance;
- D) determining a protein refractive index increment corresponding to the protein concentration of the tear sample;
- E) calculating a refractive index of the tear sample due to salinity alone by computing a difference between the measured refractive index of the tear sample and the protein refractive index increment;
- F) determining a salt concentration of the tear sample corresponding to the refractive index of the tear sample due to salinity alone; and
- G) converting the salt concentration to an osmolarity of the tear sample.

20. The method according to claim 19, further comprising the step of placing the tear sample in contact with a surface, wherein the step of measuring an optical absorbance of the tear sample and the step of measuring a refractive index of the tear sample are both performed while the tear sample is in contact with the surface.

21. The method according to claim 19, wherein the step of determining a protein concentration of the tear sample corresponding to the measured absorbance includes comparing the measured absorbance to a predetermined relationship between optical absorbance and protein concentration for a standard protein solution.

22. The method according to claim 19, wherein the step of determining a protein refractive index increment corresponding to the protein concentration of the tear sample includes comparing the protein concentration of the tear sample to a predetermined relationship between protein concentration and refractive index for a standard protein solution to find a refractive index corresponding to the protein concentration of the tear sample, and subtracting a known refractive index of water from the refractive index corresponding to the protein concentration of the tear sample.

23. The method according to claim 19, wherein the step of determining a protein refractive index increment corresponding to the protein concentration of the tear sample includes comparing the protein concentration of the tear sample to a predetermined relationship between protein concentration and protein refractive index increment for a standard protein solution.

24. The method according to claim 19, wherein the step of determining a salt concentration of the tear sample corresponding to the refractive index of the tear sample due to salinity alone includes comparing the refractive index of the tear sample due to salinity alone to a predetermined relationship between refractive index of a standard saline solution and salt concentration of the saline solution.

25. The apparatus according to claim 1, wherein the absorbance detection system is configured to direct a light beam in a direction perpendicular to a transparent surface contacted by the tear sample.

26. The apparatus according to claim 1, wherein the absorbance detection system includes a first light source, and the refractometer system includes a second light source at a different location from the first light source.

* * * * *